United States Patent [19]

Collison et al.

[11] Patent Number: 4,834,101

[45] Date of Patent: May 30, 1989

[54] CATHETER-TYPE ELECTROCHEMICAL SENSORS

[75] Inventors: Michael E. Collison; Mark E. Meyerhoff, both of Ann Arbor, Mich.

[73] Assignee: The University of Michigan, Ann Arbor, Mich.

[21] Appl. No.: 67,320

[22] Filed: Jun. 26, 1987

[51] Int. Cl.$^4$ .............................................. A61B 5/00
[52] U.S. Cl. .................................. 128/635; 204/403; 204/415; 204/431; 204/433
[58] Field of Search ................ 128/635; 204/403, 415, 204/431, 433

[56] References Cited

U.S. PATENT DOCUMENTS

| | | | |
|---|---|---|---|
| 3,898,147 | 8/1975 | Niedrach | 128/635 |
| 3,900,382 | 8/1975 | Brown, Jr. | 204/195 M |
| 3,911,901 | 10/1975 | Niedrach et al. | 128/635 |
| 3,923,626 | 12/1975 | Niedrach et al. | 204/195 R |
| 3,926,766 | 12/1975 | Niedrach et al. | 204/195 P |
| 3,957,613 | 5/1976 | Maeur | 128/635 |
| 4,197,852 | 4/1980 | Schindler et al. | 128/635 |
| 4,197,853 | 4/1980 | Parker | 128/635 |
| 4,486,290 | 12/1980 | Cahalan et al. | 128/635 |
| 4,508,598 | 4/1985 | Giner | 128/635 |
| 4,519,973 | 5/1985 | Cahalan et al. | 264/267 |
| 4,534,355 | 8/1985 | Potter | 128/635 |
| 4,565,665 | 1/1986 | Fogt | 264/267 |
| 4,565,666 | 1/1986 | Cahalan et al. | 264/267 |
| 4,600,495 | 7/1986 | Fogt | 204/409 |
| 4,653,499 | 3/1987 | Murray, Jr. et al. | 128/635 |

*Primary Examiner*—Lee S. Cohen
*Attorney, Agent, or Firm*—Rohm & Monsanto

[57] ABSTRACT

A dual lumen $CO_2$ catheter is formed of medical grade dual lumen silicone rubber tubing which has been impregnated with tridodecyl amine. The silicone tubing is gas permeable, and an external reference electrode is used to monitor the potential across the impregnated outer wall of the dual lumen tubing as a function of pH. The analyte to be monitored is selected from the group consisting of $CO_2$, $NH_3$, $SO_2$, $NO_2$, $H_2S$, and $HCN$, the internal reference and electrolyte solutions contained in the lumens being selected in response to the particular analyte desired to be monitored. In a $CO_2$ embodiment, the reference lumen is filled with a buffered internal reference solution, and the response lumen is filled with a bicarbonate filling solution. Reference wires formed of Ag/AgCl in respective ones of the lumens forms the internal electrodes.

9 Claims, 5 Drawing Sheets

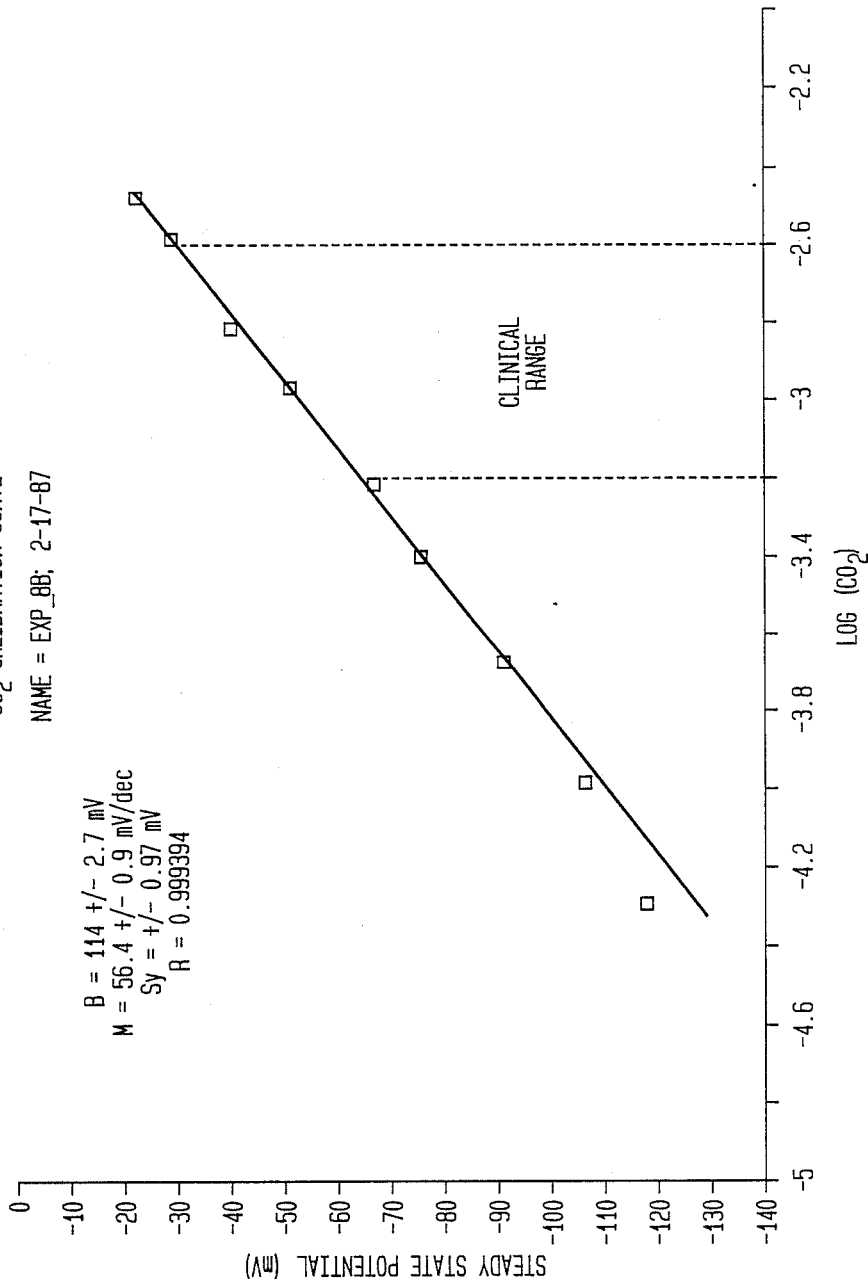

CATHETER-TYPE ELECTROCHEMICAL SENSORS

BACKGROUND OF THE INVENTION

This invention relates generally to chemical sensors, and more particularly, to a catheter-type potentiometric gas sensor suitable for continuous in vivo blood gas monitoring.

The knowledge of gas levels in blood is essential for the accurate assessment of the respiratory and acid-base status of a patient. Oxygen and carbon dioxide, the respiratory gases, are of fundamental importance since their partial pressures, $pO_2$ and $pCO_2$, are useful in determining cardiopulmonary homeostasis, or the ability of the cardiopulmonary system to maintain a delicate balance between the body's respiratory $CO_2$ production and its $O_2$ consumption. Additionally, the partial pressure of carbon dioxide in blood and the dissolved bicarbonate anion are the two principle factors which govern the pH of the blood. The measurement of two of these three parameters, such as pH and partial pressure of carbon dioxide, will completely characterize the acid-base state of the blood.

Commercially available blood gas analyzer systems typically monitor three analytes, including blood pH, the partial pressure of carbon dioxide, and the partial pressure of oxygen. Such monitoring provides a clinician with a complete determination of the respiratory and acid-base status of a patient.

In conventional discrete blood gas analyzers, the partial carbon dioxide pressure level in blood is most commonly obtained by drawing a discrete arterial blood sample which is then analyzed by a conventional Severinghaus carbon dioxide sensor housed in an automated blood gas analyzer. At least a two to three minute time lag between the drawing of a sample and the recording of the value of the partial pressure of carbon dioxide, is inherent in the known discrete sampling arrangement. However, in many diagnostic situations, such as emergency, surgical, and critical care patients, blood gas levels can change abruptly, illustratively within minutes, thereby indicating eminent respiratory or metabolic failure. In such situations, a clinician working with a discrete blood gas analyzer is required to make frequent blood gas measurements so as to diagnose accurately the patient's rapidly changing condition. Thus, a major disadvantage of the known method is the high expense associated with the maintenance of a sufficient number of blood gas analyzers, and the providing of a staff of trained personnel to perform the frequent blood gas measurements. More importantly, improper collection and/or handling of a blood sample prior to analysis can produce error in the discrete blood gas determination. It is evident from the foregoing that the time lag which is inherent in the discrete sampling system limits the speed of diagnosis, and consequently the implementation of corrective treatment. Accordingly, intensive research has been conducted over the past decade, devoted to the search for methods which allow for the continuous monitoring of arterial blood gas tensions.

A variety of technologies has been applied to the development of continuous blood sensors for the partial pressure of carbon dioxide. The monitoring of partial pressures of carbon dioxide can involve invasive and noninvasive approaches. Conventional gas sensors have been used in noninvasive extracorporeal loops and transcutaneous arrangements. Invasive gas sensing probes have been based on mass spectrometry, conductivity, gas chromatography, potentiometry, and fiber optic systems. Although each of these developments has some merit, none has achieved wide clinical application.

One prior art system is an extracorporeal loop device which continuously draws arterial blood which is then circulated through appropriate tubing to external sensing devices; the blood then being returned to a vein elsewhere in the body of the patient. Typically, the external sensing devices incorporate sensors for oxygen, carbon dioxide, and pH measurements. It is a problem with all extracorporeal systems that the patient must be heparinized to prevent blood clotting in the loop or on the sensors, and to prevent loose blood clots from causing vascular occlusion or strokes. Heparinization increases the risk of post-operative complications in surgical patients since necessary clotting mechanisms are inhibited. Additional drawbacks of extracorporeal devices include losses of carbon dioxide in the loop tubing, the need for elaborate temperature control, and the increased risk of infection. Consequently, extracorporeal loops are rarely used for blood gas measurements.

Non-invasive transcutaneous blood gas sensors were developed in the early 1970's In this known system, heated conventional gas sensors are placed directly on the skin of the patient such that the partial pressure of gases diffusing to the skin surface can be measured. This diffusion of gases from the subcutaneous arteries to the skin surface is dependent upon skin thickness, blood flow, tissue concentration and/or expiration, and arterial gas concentration. In infants, the factors balance, such that the transcutaneous blood gas values approximate the arterial values. There is, however, a wide variation in adult skin thickness which leads to incorrect predictions of arterial blood gas levels from transcutaneous measurements. Inaccurate predictions of arterial blood gas levels will also occur in patients with reduced blood flow from injury or illness. Thus, transcutaneous blood gas monitoring is clinically accepted for infants, but rarely is applied to adults.

A known invasive system involves in vivo mass spectrometric blood gas analysis. This system was first proposed in 1966 and has since been pursued by a number of researchers. The basic configuration requires the use of a mass spectrometer, an in vivo sampling probe, and associated connecting tubing. A significant limitation of this technique is the complexity and cost of mass spectrometer instrumentation relative to that of electrochemical sensors. The major drawback to mass spectrometric probe measurements is the non-equilibrium flow dependent, or diffusion limited nature of the gas sampling probe. The mass spectrometer maintains the sampling probe at a negative pressure that withdraws gases from the surrounding blood stream. Under low blood flow conditions, the extraction of gases by the probe may deplete the adjacent blood of analyte causing erroneously low results. Moreover, blood clotting and/or protein build-up on the probe can impede the diffusion of gases into the probe, thereby yielding false blood gas values. Thus, economic factors and non-equilibrium sampling effects account for the limited biomedical application of mass spectrometric blood gas analysis.

Similarly, flow dependent conductivity-based carbon dioxide catheters have been described for in vivo applications. These catheters, however, are non-selective and suffer the same non-equilibrium disadvantages as the mass spectrometric probes. Gas chromatography has also been applied to continuous blood gas monitoring. Blood gases diffuse into the body of an indwelling catheter probe where they approach their equilibrium concentration with a bolus of carrier gas (He) contained therewithin. At fixed intervals, illustratively between three and four minutes, the bolus is flushed through the gas analyzer unit for separation and measurement. Thus, the gas chromatographic probes do not sample continuously, but rather an automated analysis is performed every four minutes. The disadvantages of this approach include the delicate nature of the probe and its associated high failure rate. More importantly, a commercial implementation of this approach will yield serious inaccuracies, on the order of between 10 and 20 per cent, in blood gas determinations.

In recent years, fiber optic carbon dioxide sensors have been developed. This approach offers several advantages including true equilibrium measurements of partial carbon dioxide, lack of electrical connections to the patient, and ease of miniaturization of fiber optic devices. Despite the promise of fiber optic designs, difficulties with sensor drift appear to have limited its utility in vivo applications in measuring the partial pressure of carbon dioxide. The drift has been attributed to changes in optical path length caused by deformation of the sensor tip while it is in the blood vessel.

The development of intravascular electro-based probes for the measurement of partial pressure of carbon dioxide has centered primarily on the miniaturization of the known Severinghaus sensor. FIG. 1 is a comparative schematic representation of Severinghaus-type ammonia ($NH_3$) and carbon dioxide ($CO_2$) gas sensors. As shown in the drawing, sodium sensor 10 and carbon dioxide sensor 11 are each combination electrodes in that they monitor pH levels also. Each of the sensors is provided with a respective one of pH electrodes 12 and 13. Electrode 12 is filled with $NH_3$ and electrode 13 is filled with carbon dioxide. Such electrodes are arranged in an internal electrolyte and are separated therefrom by respective glass membranes 14 and 15. A gas permeable membrane separates the internal electrolyte from the substance being monitored, illustratively blood (not shown).

Since Severinghaus sensors are potentiometric devices, measurements are made essentially under zero-current conditions so that no analyte carbon dioxide is consumed by the measurement process. Thus, true equilibrium measurements are made and problems associated with mass transfer of carbon dioxide, such as blood flow variations and carbon dioxide diffusion limitations, should not cause errors in the partial pressure values of carbon dioxide which are determined. In addition, all Severinghaus-type carbon dioxide devices are unaffected by anaesthetic gases.

The design of the system of FIG. 1 employs miniaturized glass pH electrodes as internal sensing elements in catheter size devices. However, such arrangements are hampered by the fragility, noise, and cost associated with the electrodes. The prior art has thrust at the problem associated with miniature glass electrodes, by providing sensors which detect the partial pressure of carbon dioxide based on quinhydrone and antimony pH sensitive electrode systems. These sensors, however, suffer from the disadvantages of oxygen sensitivity, instability, and large size. Thus, they do not appear to be suitable for in vivo testing.

FIG. 2 is a schematic representation of a prior art combination sensor 20 which monitors pH and the partial pressure of carbon dioxide. This known probe is comprised of a palladium oxide pH electrode 21, a Ag-/AgCl reference electrode 22 and a bicarbonate electrolyte 23 housed behind a gas-permeable membrane 64 which contains a mobile hydrogen ion carrier which makes the membrane permeable to hydrogen ions. The partial pressure of carbon dioxide is measured by monitoring the voltage between the two internal electrodes, while the sample pH is measured between the Pd/PdO electrode 21 and an external reference electrode (not shown). Sensor 20 measures 0.9 mm in outside diameter. It is a disadvantage of this type of sensor that they are poorly flexible, exhibiting a decrease in sensitivity when the sensor is bent. This type of sensor also drifts unacceptably unless recalibrated every 1.5 hours. The drift is attributed to the PdO electrode's sensitivity to redox species. In addition, the sensor is also very sensitive to temperature changes, as might occur during fever or hypothermia. As a result of this, this combination sensor has seen only limited use.

FIG. 3 is a schematic representation of a catheter sensor 30 which measures the partial pressure of carbon dioxide and is based on a tubular polymeric membrane internal pH electrode. In this known arrangement, a pH sensitive membrane 31 is situated safely within the wall of the internal tubing, rather than at the vulnerable tip of the sensor. This protects the sensing regions from damage during catheter placement or removal. In addition, this geometry allows for sensor size reduction without a corresponding decrease in the pH sensitive membrane area and a concomitant increase in electrode resistance. Also noteworthy is the heightened rate of flexibility afforded by the polymer based internal pH electrode. Finally, since the internal electrode is based on a hydrogen ion permselective polymer membrane, the sensor is virtually insensitive to sample redox species.

Although this design is promising for continuous in vivo monitoring of the partial pressure of carbon dioxide, there are difficulties in its fabrication which will limit its application.

It is, therefore, an object of this invention to provide a simple and economical sensor which provides determination of the respiratory and acid-base status of a patient.

It is another object of this invention to provide an implantable sensor for continuous monitoring of blood carbon dioxide partial pressures.

It is also an object of this invention to provide a single catheter implant which can monitor pH and the partial pressure of carbon dioxide simultaneously.

It is additionally an object of this invention to provide a blood gas analyzer system which does not require trained personnel to be operated.

It is a further object of this invention to provide a blood gas analysis system which reduces the possibility of error resulting from faulty collection and/or handling of a blood sample.

It is still another object of this invention to provide a blood gas analysis sensor which eliminates lag time between samplings.

It is a yet further object of the invention to provide a blood gas monitoring arrangement which eliminates the need to heparinize a patient.

it is also a further object of this invention to provide a blood gas sensor which is not plagued by drift.

It is yet another object of this invention to provide a blood gas sensor which is not fragile and does not have a high failure rate.

SUMMARY OF THE INVENTION

The foregoing and other objects are achieved by this invention which provides an arrangement for in vivo monitoring of the concentration of blood gases. The arrangement is constructed to have an elongated body which is itself formed of a gas-permeable polymeric material impregnated with a pH sensitive material. Such impregnation is effected over a predetermined portion of the elongated body, thereby forming a pH responsive membrane. In accordance with the invention, the elongated body is provided with at least one a lumen therein for accommodating a predetermined solution. A sensor electrode is arranged in said lumen of the elongated body for communicating electrically with the predetermined solution for detecting an electric potential.

The inventive sensor can be operated in combination with a reference electrode external to the elongated body. This external electrode facilitates monitoring of the potential across the impregnated outer wall of the elongated body, which is formed of a silicone rubber, the potential being a function of the pH of the sample being monitored. In a specific illustrative embodiment of the invention, the outer wall of the elongated body is impregnated with tridodecyl amine.

The particular solution installed in the lumen is selected in response to a predetermined analyte being monitored, which may illustratively be from the group consisting of $CO_2$, $NH_3$, $SO_2$, $NO_2$, $H_2S$, and $HCN$.

In a preferred embodiment of the invention, the sensor electrode is in the form of a wire of Ag/AgCl. The sensor electrode is in electrical communication with the solution in the lumen.

In accordance with a highly advantageous embodiment of the invention, the elongated body is provided with a further lumen therein, and there is additionally provided a further sensor electrode arranged in the further lumen for communicating electrically with a second predetermined solution. The second predetermined solution is a bicarbonate solution, which comprises 0.025 M $NaHCO_3$ and 0.1M NaCl.

In the dual lumen embodiment, the elongated body means is formed of a gas-permeable polymeric material impregnated with a pH sensitive material over a predetermined portion thereof for forming a pH responsive membrane. The elongated body has first and second lumens therein for accommodating respective ones of first and second predetermined solutions. There is additionally provided the use of first and second sensor electrode means of Ag/AgCl for communicating electrically with respective ones of said predetermined solutions for detecting at least one electric potential.

BRIEF DESCRIPTION OF THE DRAWING

Comprehension of the invention is facilitated by reading the following detailed description in conjunction with the annexed drawings, in which:

FIG. 5 is a graphical representation of a carbon dioxide calibration curve.

DETAILED DESCRIPTION

Figure 1:
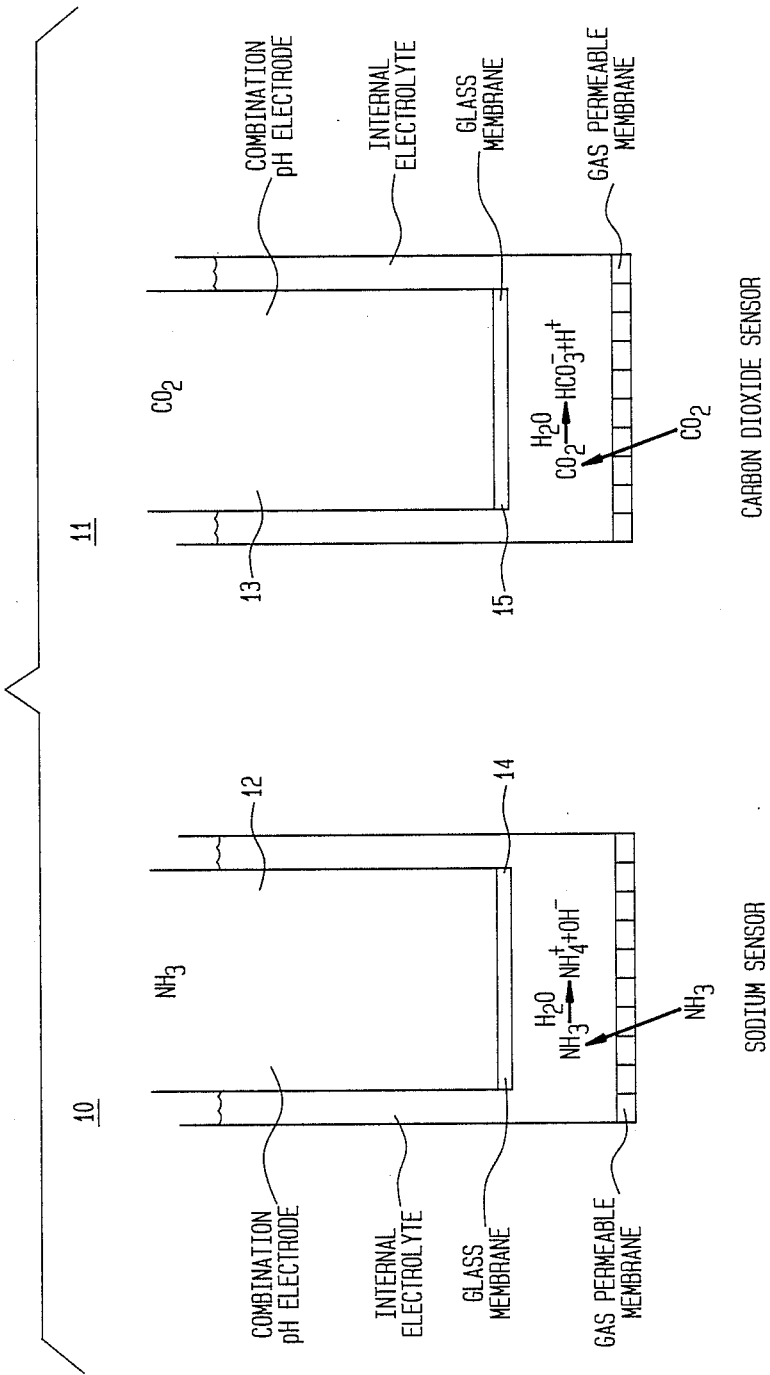
FIG. 1 is a comparative schematic representation of prior art Severinghaus-type ammonia ($NH_3$) and carbon dioxide ($CO_2$) gas sensors.
Figure 2:
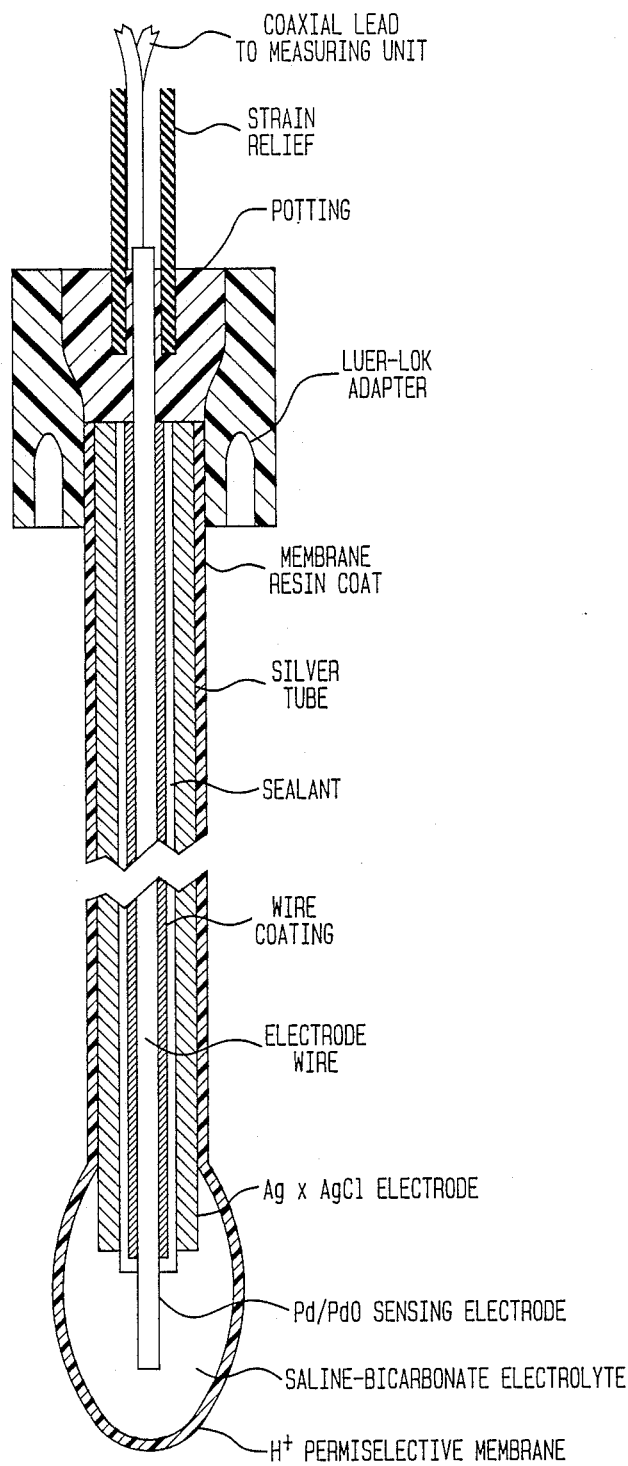
FIG. 2 is a schematic representation of a prior art combination sensor which monitors pH and the partial pressure of carbon dioxide.
Figure 3:
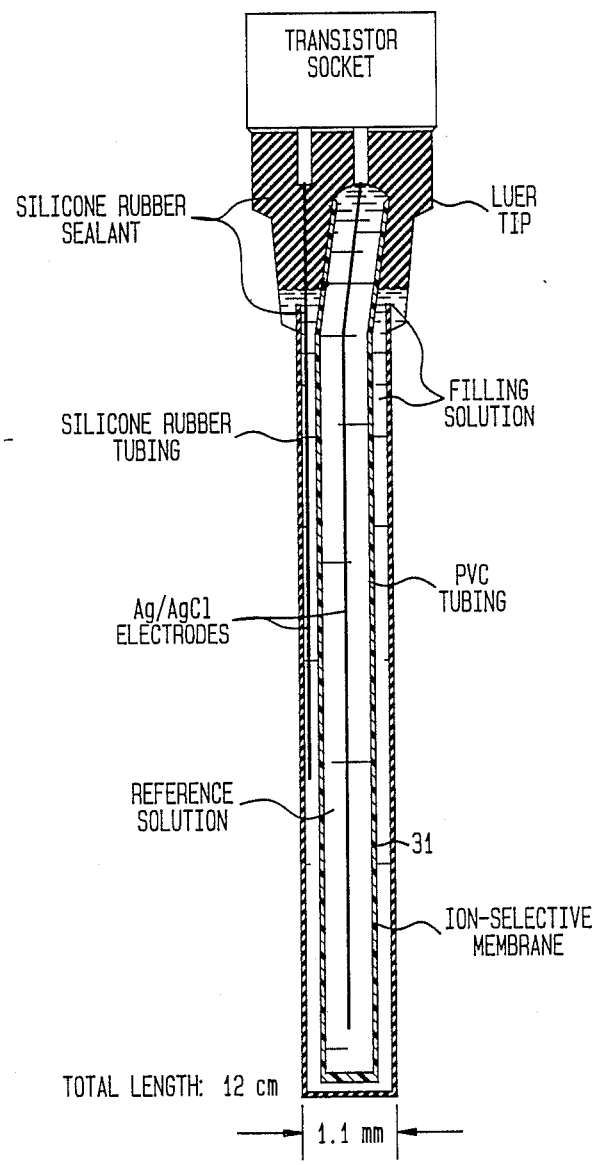
FIG. 3 is a schematic representation of a prior art catheter sensor which measures the partial pressure of carbon dioxide and is based on a tubular polymeric membrane internal pH electrode.
Figure 4:
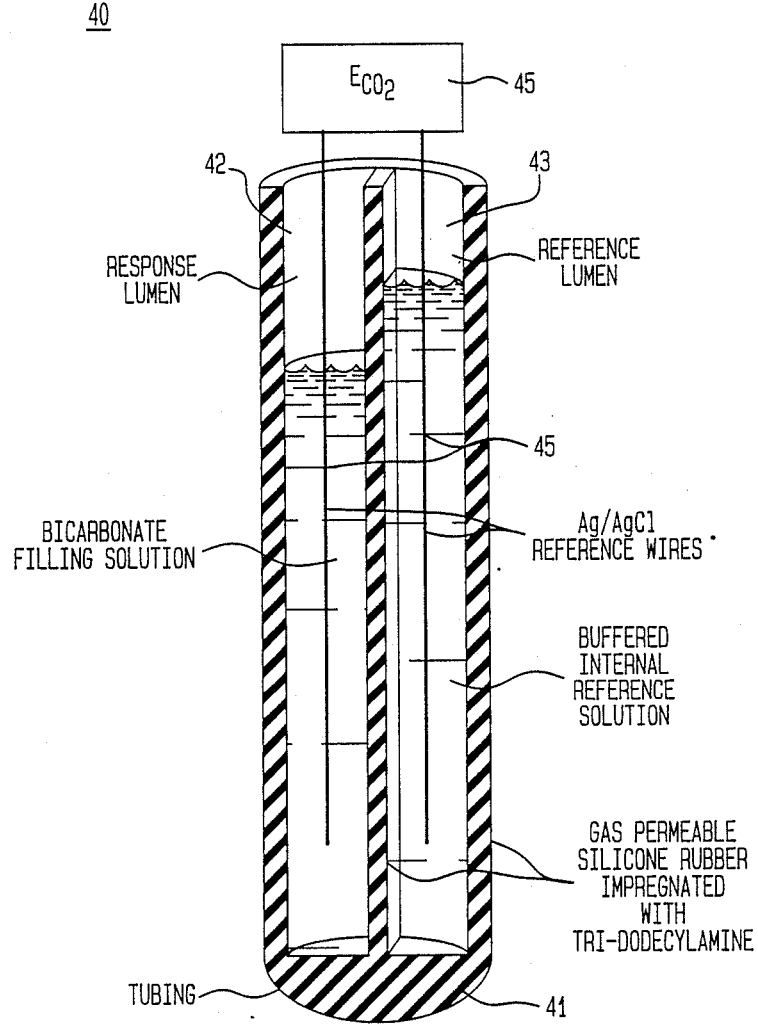
FIG. 4 is a schematic representation of a dual lumen catheter sensor constructed in accordance with the principles of the invention.

FIG. 4 is a schematic representation of a dual lumen catheter sensor 40 constructed in accordance with the principles of the invention. As shown in the figure, sensor 40 is constructed using dual lumen tubing 41 having a lumen 42 which is filled with a bicarbonate solution, and a lumen 43 which is filled with a buffered internal reference solution. In one specific embodiment, tubing 41 comprises an 11 cm section of Dow Corning Silastic Rx50CT medical grade dual lumen tubing, having 1.14 mm outside diameter and 0.15 mm wall thickness. In accordance with the invention, the medical grade tubing is immersed approximately 2 cm in a hydrogen ion carrier impregnating solution, such as tridodecyl amine (TDDA), for two minutes or until swelling of the tubing is visible. The impregnating solution may be, in certain embodiments, 0.5 g TDDA in 2.5 ml xylene.

The swollen tubing section is allowed to dry in air, illustratively for an overnight period, after which any solution remaining in the tubing lumens is expelled with compressed air. A short section of approximately between 2 to 5 mm of the impregnated end of the tubing is plugged in both lumens with silicone rubber adhesive which is allowed to cure for at least one hour. Lumen 42 is filled with bicarbonate filling solution, illustratively of 0.025M $NaHCO_3$ and 0.1M NaCl. The buffered internal reference solution in lumen 43 is, in one embodiment, comprised 0.80M phosphate buffer (pH 7.0) containing 0.10M NaCl. Preferably, the compositions of the buffered reference solution and the bicarbonate fill solution are optimized to match the osmolarity of blood in order to improve the long-term stability of the sensor.

Each of lumens 42 and 43 contains an associated one of Ag/AgCl reference wires 45. In a one embodiment, the Ag/AgCl leads are soldered to a transistor socket 45. The area between the top of the silicone rubber tubing and the transistor socket is encapsulated in silicone rubber adhesive (not shown) to prevent the Ag/Agcl leads from shorting. Measurements are then made by connecting the sensor's transistor socket leads to a pH meter and monitoring the potential of the electrochemical cells.

The configuration of sensor 40 improves upon the miniaturized Severinghaus sensors described hereinabove by forming an internal pH responsive membrane in the wall of the dual lumen carbon dioxide permeable rubber tube. This design eliminates the need for a separate internal pH responsive electrode which greatly simplifies the construction of the sensor. Moreover, the elimination of the separate internal pH responsive electrode permits reductions in sensor dimensions.

The sensor design of FIG. 4 may be readily adapted to detect hydrogen ions and $CO_2$ gas simultaneously. This is effected merely by contacting the sample with an appropriate external reference electrode, whereby the potential across the outer, TDDA-impregnated wall of the dual lumen can be monitored as a function of sample pH. Thus, the potential between the two inner reference Ag/AgCl wires would track the partial pressure of carbon dioxide in the sample while the potential between the Ag/AgCl wire of the reference lumen and the external reference electrode would track the sample pH. Such an arrangement would facilitate continuous, real-time monitoring of two of the three blood gas analytes (blood $pCO_2$ and pH).

In alternative embodiments, the wall between the lumens in the dual-lumen tubing, after being impregnated with the hydrogenion carrier TDDA can serve as the pH selective membrane. In such embodiments, the potential across this inner tubing wall can be correlated to the pH of the bicarbonate filling solution as a function of the partial pressure of carbon dioxide in the sample. This embodiment provides reduced fabrication complexity and improved potential for miniaturization of the sensor dimensions. More significantly, such elimination of the inner pH responsive tubing may permit complete automation of fabrication of duallumen catheter-based sensors.

FIG. 5 is a graphical representation of a carbon dioxide calibration curve. As shown in this figure, the logarithm of the carbon dioxide concentration is plotted against the steady state potential at the output of the sensor. The plotted results were obtained from in vitro studies wherein standard additions of sodium bicarbonate were made to an acidic sample buffer solution at 37° C. The results recorded are the equilibrium potential of the dual lumen sensor shown schematically in FIG. 4. Reference to FIG. 5 shows that the dual lumen sensor exhibits nearNernstian sensitivity (92%) from 5 to 130 torr $pCO_2$ ($1.6 \times 10^{-4}$ to $4.0 \times 10^{-3}$M $CO_2$). This range of Nernstian response covers the entire clinical $pCO_2$ range which is approximately 15-84 torr.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and descriptions in this disclosure are proffered to facilitate comprehension of the invention and should not be construed to limit the scope thereof.

What is claimed is:

1. An arrangement for monitoring concentration of an analyte selected from the group consisting of $CO_2$, $NH_3$, $SO_2$, $NO_2$, $H_2S$, and HCN, the arrangement comprising:

elongated body means having dual lumens separated from one another by an integrally formed interlumen wall, said elongated body means being formed of a gas-permeable polymeric material impregnated with a pH sensitive material over at least a portion thereof for forming a pH responsive membrane, said elongated body means having a first one of said dual lumens therein accommodating an electrolyte solution responsive to a selected one of the analytes, a second one of said dual lumens accommodating a reference solution, and an ion sensitive membrane arranged as said integrally formed interlumen wall between said first and second ones of said dual lumens; and first and second sensor electrode means arranged in respective ones of said first and second ones of said dual lumens of said elongated body means for communicating electrically with respective ones of said electrolyte solution and said reference solution for detecting an electric potential.

2. The arrangement of claim 1 wherein said pH sensitive material is tridodecyl amine.

3. The arrangement of claim 1 wherein said polymeric material is a silicone rubber.

4. The arrangement of claim 1 wherein said first and second sensor electrode means are formed of Ag/AgCl.

5. The arrangement of claim 1 wherein and electrolyte solution further comprises a bicarbonate solution, comprising 0.025M $NaHCO_3$ and 0.1M NaCl.

6. An arrangement for monitoring continuously in vivo concentration of blood gases, the arrangement comprising:

elongated body means formed of a gas-permeable polymeric material impregnated with a pH sensitive material over a predetermined portion thereof for forming a pH responsive membrane, said elongated body means having first and second lumens therein accommodating respective ones of a buffered internal reference solution and a bicarbonate filling solution, said first and second lumens being an ion communication with one another via an integrally formed gas permeable membrane interposed therebetween; and first and second sensor electrode means arranged in respective ones of said first and second lumens of said elongated body means for communicating electrically with respective ones of said buffered internal reference and said bicarbonate filling solutions for detecting at least one electric potential.

7. The arrangement of claim 6 wherein said first and second sensor electrode means are formed of Ag/AgCl.

8. The arrangement of claim 6 wherein said gas permeable polymeric material of which said elongated body means is formed is silicone rubber.

9. The arrangement of claim 6 wherein said pH sensitive material is tridodecyl amine.

* * * * *

UNITED STATES PATENT AND TRADEMARK OFFICE
CERTIFICATE OF CORRECTION

PATENT NO. : 4,834,101

DATED : May 30, 1989

INVENTOR(S) : Collison, et. al.

It is certified that error appears in the above-identified patent and that said Letters Patent is hereby corrected as shown below:

Column 1, between the Title and the Heading "Background of the Invention", please insert the following paragraph:

-- Government Rights

This invention was made with Government support under Grant No. GM28882 awarded by the National Institutes of Health. The Government has certain rights in the invention.

Signed and Sealed this

Fifteenth Day of December, 1992

Attest:

DOUGLAS B. COMER

*Attesting Officer*       Acting Commissioner of Patents and Trademarks